United States Patent [19]

Lang

[11] Patent Number: 5,138,099
[45] Date of Patent: Aug. 11, 1992

[54] SYNTHESIS OF FLUOROBENZALDEHYDES

[75] Inventor: John F. Lang, Webster Groves, Mo.

[73] Assignee: Mallinckrodt Specialty Chemicals Company, St. Louis, Mo.

[21] Appl. No.: 738,625

[22] Filed: Jul. 31, 1991

[51] Int. Cl.$^5$ .................. C07C 45/45; C07C 47/55
[52] U.S. Cl. ............................ 568/435; 568/425; 568/426; 568/437
[58] Field of Search ............ 568/435, 437, 438, 426, 568/425, 434

[56] References Cited

U.S. PATENT DOCUMENTS

4,588,844  5/1986  Kysela et al. ............... 568/41
4,845,304  7/1989  Yoshida et al. ............. 568/437

FOREIGN PATENT DOCUMENTS

7028183  11/1969  Japan ........................... 568/437

OTHER PUBLICATIONS

Lewin et al., "Formulation of Arenes by . . . Procedures", *Organic Preparations and Procedures Int.*, 10(5), 201–204 (1978).
Aslam et al., "Friedel–Crafts Acylations . . . Gattermann Formylation Reactions", *J.C.S. Perkin 1*, pp. 892–894.

*Primary Examiner*—Werren B. Lone
*Attorney, Agent, or Firm*—Rothwell, Figg, Ernst, & Kurz

[57] ABSTRACT

4-fluorobenzaldehydes are formed from compounds of the formula (I)

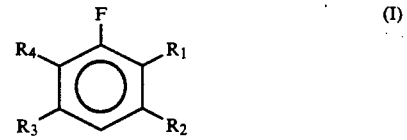

wherein $R_1$, $R_2$, $R_3$ and $R_4$ are the same or different, and represent H, halogen, or an alkyl group of from 1 to about 10 carbon atoms, wherein, when at least one of $R_1$, $R_2$, $R_3$ or $R_4$ is halogen, at least one of remaining $R_1$, $R_2$, $R_3$ or $R_4$ is alkyl. the compound of formula of (I) is reacted with a formylating agent in the presence of $FeCl_3$ in a reaction mixture, from which is separated a compound of the formula (II)

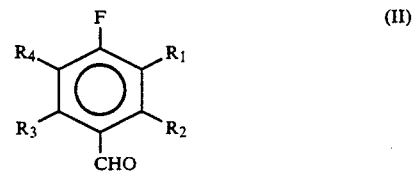

wherein $R_1$, $R_2$, $R_3$ and $R_4$ are as defined above.

26 Claims, No Drawings

SYNTHESIS OF FLUOROBENZALDEHYDES

BACKGROUND OF THE INVENTION

1. Field of the Invention

The present invention relates to formylation of benzene derivatives so as to form fluorobenzaldehydes.

2. Description of the Background Art

Fluorobenzaldehydes are useful as intermediates for the synthesis of various dyes, herbicidal compounds, pharmaceuticals and the like.

There are several well-known methods for electrophilically formylating arenes which contain activating (electron-donating) substituents, but these either fail completely or are impractical for arenes which contain electron withdrawing substituents such as fluorine. Although little work has been done with alpha, alpha-dichloromethyl alkyl ethers as formylating agents, certain benzene derivatives which contain mildly activating ring substituents have previously been formylated using dichloromethyl alkyl ethers in the presence of tin chloride, titanium chloride, or aluminum chloride. Such reactions have not achieved commercial importance because the isomeric purity of the aldehyde products has been poor. Furthermore, the yields are often reduced by unwanted coupling products between the intermediates and substrate, and commercially useful quantities of dichloromethyl alkyl ethers are not readily available.

There remains a need in the art for methods of synthesizing fluorobenzaldehydes in high isomeric purity, and for new fluorobenzaldehyde compounds.

SUMMARY OF THE INVENTION

In accordance with the present invention, a process for synthesizing 4-fluorobenzaldehydes, comprises providing a compound of the formula (I)

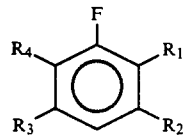

(I)

wherein $R_1$, $R_2$, $R_3$ and $R_4$ can be the same or different, and represent H, halogen, or an alkyl group of from 1 to about 10 carbon atoms, wherein, when at least one of $R_1$, $R_2$, $R_3$ or $R_4$ is halogen, at least one of remaining $R_1$, $R_2$, $R_3$ or $R_4$ is alkyl. A reaction mixture is formed of the compound of formula (I) and a formylating agent in the presence of $FeCl_3$. From the reaction mixture is separated a compound of the formula (II)

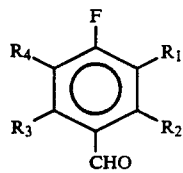

(II)

wherein $R_1$, $R_2$, $R_3$ and $R_4$ are as defined above. The invention further relates to compounds of the formula (II) wherein $R_1$, $R_2$, $R_3$ and $R_4$ can be the same or different, and represent H or an alkyl group of from 1 to about 10 carbon atoms, wherein at least 1 of $R_1$, $R_2$, $R_3$ or $R_4$ is alkyl, and wherein when $R_1$, $R_2$, and $R_4$ are H, $R_3$ is an alkyl group of from 2 to about 10 carbon atoms.

DETAILED DESCRIPTION OF THE PREFERRED EMBODIMENTS

A starting material for carrying out the process of the present invention is a compound of the formula (I) as defined above, wherein $R_1$, $R_2$, $R_3$ and $R_4$ can be the same or different, and represent H, a halogen such as fluorine, chlorine, bromine or the like, or an alkyl group of from 1 to about 10 carbon atoms wherein, when at least one of $R_1$, $R_2$, $R_3$ or $R_4$ is halogen, at least one of remaining $R_1$, $R_2$, $R_3$ or $R_4$ is alkyl.

A reaction mixture is formed of the compound of formula (I) as defined above, and a formylating agent in the presence of an $FeCl_3$ catalyst (which advantageously is anhydrous). From the reaction mixture is separated a 4-fluorobenzaldehyde of the formula (II) as set forth above, wherein $R_1$, $R_2$, $R_3$ or $R_4$ are as previously defined.

In the process of the present invention, the position of the fluorine on the benzene ring in formula (I) directs the positioning of the aldehyde group (—CHO) to the 4-position, so long as substituents $R_1$, $R_2$, $R_3$ and $R_4$ do not interfere.

When $R_1$, $R_2$, $R_3$ and/or $R_4$ are alkyl groups, they can be straight chain or branched. In preferred embodiments, when $R_1$, $R_2$, $R_3$ and/or $R_4$ are alkyl groups, the number of carbon atoms therein are from 1 to about 5, more preferably, from 1 to about 3 and even more preferably about 2 or 3 carbon atoms.

In accordance with one embodiment, one of $R_1$, $R_2$, $R_3$ or $R_4$ is an alkyl group, and the remainder of $R_1$, $R_2$, $R_3$ and $R_4$ are H.

In a preferred embodiment, one of $R_2$ or $R_3$ is methyl and meta to F in formula (I), and the remainder of $R_1$, $R_2$, $R_3$ or $R_4$ are H.

In another preferred embodiment, one of $R_1$ or $R_4$ is methyl and ortho to F in formula (I), and the remainder of $R_1$, $R_2$, $R_3$ and $R_4$ are H.

In preferred embodiments, the formylating agent with which the compound of formula (I) is reacted, is selected from the group consisting of dichloromethyl alkyl ethers, dichloromethyl alkanoates (e.g., acetates), and dichloromethyl benzoate. In particularly preferred embodiments, the formylating agent is a dichloromethyl alkyl ether, most preferably dichloromethyl methyl ether.

According to one aspect of the invention, a dichloromethyl alkyl ether formylating agent is provided by reacting $PCl_5$ with an alkyl formate at about room temperature so as to form about an equimolar mixture of the corresponding dichloromethyl alkyl ether and phosphorus oxychloride ($POCl_3$). This mixture is reacted with a compound of formula (I) in the presence of the catalyst $FeCl_3$. Hydrolysis of the mixture with water forms the corresponding compound of formula (II). The dichloromethyl alkyl ether preferably is separated from the phosphorous oxychloride by distillation prior to use, but even the equimolar mixture can serve as a formylation agent by the addition of additional $FeCl_3$. Any $POCl_3$ remaining can be separated from the compound of formula (II) by hydrolysis of the $POCl_3$.

In one embodiment, the compound of formula (1) is reacted with the formylating agent in the presence of catalyst $FeCl_3$. In compounds of formula (I) where formylation results in an isomeric mixture of intermediates, the addition of an electrophilic reagent to the reaction mixture, which already contains catalytic FeCl₃, results in selective isomeric enrichment. In a preferred embodiment, the reagent is bromine. Despite the elevated temperature typically required, minimal unwanted side products are formed when bromine is used in the presence of FeCl₃.

In accordance with one embodiment, the reaction of a compound of formula (I) so as to form a compound of the formula (II) takes place in the presence of a halogenated solvent diluent, such as methylene chloride. However, it is not necessary to utilize a halogenated solvent as a diluent, as the formula (I) substrate itself can serve as the diluent.

In accordance with one embodiment, a reaction mixture is formed between the compound of formula (I) and FeCl₃, to which is added a dichloromethyl alkyl ether at a temperature between about −20° C. and 0° C. Elemental halogen (e.g. bromine) then is added to the reaction mixture, which then is heated to between about 30° C. and about 100° C., preferably to about 65° C. The reaction mixture then is subjected to hydrolysis, after which the desired 4-fluorobenzaldehyde is separated from the reaction mixture, for example by distillation.

Without being bound to any particular theory, it is believed that the FeCl₃ catalyst and the nature of the intermediates in the isomeric enrichment step are primarily responsible for the high yields of substantially isomerically pure 4-fluorobenzaldehydes according to the present invention.

The invention also relates to compounds of the formula (II) set forth above, wherein $R_1$, $R_2$, $R_3$ and $R_4$ can be the same or different, and represent H or an alkyl group of from 1 to about 10 carbon atoms, wherein at least one of $R_1$, $R_2$, $R_3$ or $R_4$ is alkyl, and wherein when $R_1$, $R_2$, and $R_4$ are H, $R_3$ is an alkyl group of from 2 to about 10 carbon atoms. Preferred inventive compounds are those wherein one or more of $R_1$, $R_2$, $R_3$ or $R_4$ is an alkyl group, and the remainder of $R_1$, $R_2$, $R_3$ and $R_4$ are H. A particularly preferred compound in accordance with the present invention is a compound of the formula (II) set forth above wherein $R_1$ is methyl and ortho to F in formula (II), and $R_2$, $R_3$ and $R_4$ are H.

The invention is further illustrated by the following examples, which are not intended to be limiting.

EXAMPLE I

About 1.4 equivalents of Dichloromethyl methyl ether was slowly added to fluorobenzene in the presence of approximately one equivalent of anhydrous ferric chloride at −5° C., with methylene chloride as diluent. The dichloromethyl methyl ether was obtained by stirring PCl₅ and methyl formate at room temperature so as to form an equimolar mixture of POCl₃ and dichloromethyl methyl ether. This was added to the fluorobenzene without purification and with additional FeCl₃.

Unwanted 2-fluorobenzaldehyde isomer was preferentially reacted with very high selectivity and minimal side reactions by introducing approximately 0.4 equivalents of elemental bromine into the reaction mixture and heating to 65° C. for three hours. Hydrolysis of the reaction mixture and distillation provided facile separation of the desired 4-fluorobenzaldehyde from the brominated ortho isomer. The POCl₃ did not interfere with the formylation process, nor did it adversely affect the subsequent isomer enrichment step. Hydrolysis effected the removal of POCl₃ prior to distillation.

EXAMPLE II

The process described in Example I was repeated substantially as described therein, except that no methylene chloride was utilized as diluent, with the fluorobenzene substrate serving as diluent. Excess fluorobenzene was removed prior to the isomeric enrichment step. The results achieved were substantially the same as in Example I.

EXAMPLE III

The process as substantially described in Example II was utilized to convert 2-fluorotoluene to 4-fluoro-3-methyl benzaldehyde, using dichloromethyl methyl ether, ferric chloride and bromine.

Since many modifications, variations, and changes in detail may be made to the described embodiments, it is intended that all matter in the foregoing description be interpreted as illustrative and not in a limiting sense.

I claim:

1. A process for synthesizing 4-fluorobenzaldehydes, comprising a) forming a reaction mixture of FeCl₃ and a compound of the formula (I)

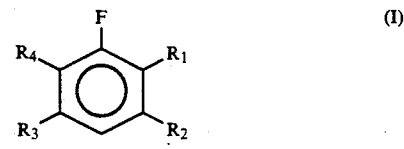

wherein $R_1$, $R_2$, $R_3$ and $R_4$ are the same or different, and represent H, halogen, or an alkyl group of from 1 to 10 carbon atoms wherein, when at least one of $R_1$, $R_2$, $R_3$ or $R_4$ is halogen, at least one of remaining $R_1$, $R_2$, $R_3$ or $R_4$ is alkyl;

b) adding a formylating agent selected from the group consisting of dichloromethyl alkyl ethers, dichloromethyl alkanoates, and dichloromethyl benzoate;

c) adding halogen to the reaction mixture and heating the reaction mixture to between about 30° C. and about 100° C.; and d) hydrolyzing the reaction mixture and separating from the reaction mixture a compound of the formula (II)

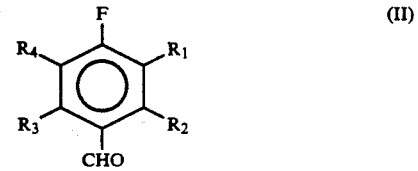

wherein $R_1$, $R_2$, $R_3$ and $R_4$ are as defined above.

2. The process of claim 1 wherein the formulating agent is an alpha, alpha-dichloromethyl alkyl ether.

3. The process of claim 1 wherein the formylating agent is a dichloromethyl alkyl ether.

4. The process of claim 3 wherein the formylating agent is dichloromethyl methyl ether.

5. The process of claim 1 wherein the formylating agent is a dichloromethyl alkyl ether, and further including the step of providing said dichloromethyl alkyl ether by reacting PCl₅ with an alkyl formate so as to form a mixture of a corresponding dichloromethyl alkyl ether and POCl$_3$.

6. The process of claim 5 wherein POCl$_3$ is removed from the the reaction mixture by hydrolysis.

7. The process of claim 1 wherein one of R$_1$, R$_2$, R$_3$ or R$_4$ is an alkyl group and the remainder R$_1$, R$_2$, R$_3$ and R$_4$ are H.

8. The process of claim 7 wherein said alkyl group has from 1 to about 5 carbon atoms.

9. The process of claim 7 wherein said alkyl group has from one to about 3 carbon atoms.

10. The process of claim 7 wherein said alkyl group has one or two carbon atoms.

11. The process of claim 7 wherein said alkyl group is methyl.

12. The process of claim 11 wherein said alkyl group is meta to F in formula (I).

13. The process of claim 11 wherein said alkyl group is ortho to F in formula (I).

14. The process of claim 1 wherein said halogen is selected from the group consisting of bromine, chlorine and iodine.

15. The process of claim 1 wherein said halogen is bromine.

16. The process of claim 1 wherein during step b), the formylating agent is added to the reaction mixture containing a methylene chloride diluent.

17. A process for synthesizing 4-fluorobenzaldehydes, comprising
a) forming a reaction mixture of FeCl$_3$ and a compound of the formula (I)

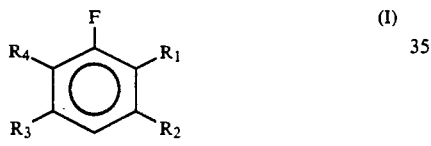

wherein R$_1$, R$_2$, R$_3$ and R$_4$ are the same or different, and represent H, halogen, or an alkyl group of from 1 to about 10 carbon atoms wherein, when at least one of R$_1$, R$_2$, R$_3$ or R$_4$ is halogen, at least one of remaining R$_1$, R$_2$, R$_3$ or R$_4$ is alkyl;
b) adding a dichloromethyl alkyl ether to the reaction mixture at a temperature between about $-20°$ C. and about $0°$ C.;
c) introducing halogen into the reaction mixture and heating the mixture to a temperature between about $30°$ C. and about $100°$ C.;
d) subjecting the reaction mixture to hydrolysis; and
e) separating from the reaction mixture a compound of the formula (II)

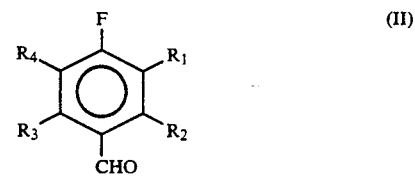

wherein R$_1$, R$_2$, R$_3$ and R$_4$ are as defined above.

18. The process of claim 17 wherein the dichloromethyl alkyl ether is provided as about an equimolar mixture of POCl$_3$ and dichloromethyl alkyl ether, said equimolar mixture being formed by mixing PCl$_5$ with a corresponding alkyl formate at about room temperature; the process further including the step of adding additional FeCl$_3$ to said reaction mixture with said equimolar mixture.

19. The process of claim 17 wherein the separation step is by distillation.

20. The process of claim 17 wherein the dichloromethyl alkyl ether is added to the reaction mixture with methylene chloride.

21. The process of claim 17 wherein the dichloromethyl alkyl ether is added to the reaction mixture at a temperature of about $-5°$ C.

22. The process of claim 17 wherein in step c), the reaction mixture is heated to about $65°$ C.

23. The process of claim 17 wherein said halogen is bromine.

24. A compound of the formula (II)

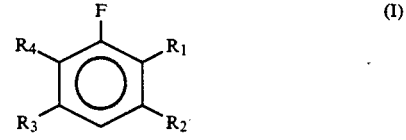

wherein R$_1$, R$_2$, R$_3$ and R$_4$ are the same or different, and represent H or an alkyl group of from 1 to about 10 carbon atoms, wherein at least one of R$_1$, R$_2$, R$_3$ or R$_4$ is alkyl, and wherein when R$_1$, R$_2$, and R$_4$ are H, R$_3$ is an alkyl group of from 2 to about 10 carbon atoms.

25. The compound of claim 24 wherein one of R$_1$, R$_2$, R$_3$ or R$_4$ is an alkyl group, and the remainder of R$_1$, R$_2$, R$_3$ and R$_4$ are H.

26. The compound of claim 25 wherein said alkyl group is methyl and ortho to F in formula (II).

* * * * *